United States Patent
Crapo et al.

(12)

(10) Patent No.: US 6,415,642 B1
(45) Date of Patent: Jul. 9, 2002

(54) DLCO CALIBRATION SYRINGE APPARATUS

(75) Inventors: Robert O. Crapo; Robert L. Jensen, both of Salt Lake City, UT (US)

(73) Assignee: Hans Rudolph, Inc., Kansas City, MO (US)

( * ) Notice: Subject to any disclaimer, the term of this patent is extended or adjusted under 35 U.S.C. 154(b) by 0 days.

(21) Appl. No.: 09/460,626

(22) Filed: Dec. 14, 1999

(51) Int. Cl.[7] .................. G01N 33/497; A61B 5/08; A61B 5/097

(52) U.S. Cl. ........................... 73/1.05; 73/1.06

(58) Field of Search .................. 73/1.05, 1.06

(56) References Cited

U.S. PATENT DOCUMENTS

| | | |
|---|---|---|
| 3,948,604 A | 4/1976 | Hoppesch |
| 4,083,367 A | 4/1978 | Portner |
| 4,278,636 A | 7/1981 | Voigt et al. ................. 422/84 |
| 4,680,956 A | 7/1987 | Huszczuk |
| 5,022,406 A | 6/1991 | Tomlinson |
| 5,119,825 A | 6/1992 | Huhn ................. 137/861 X |
| 5,193,551 A | 3/1993 | Pilipski |
| 5,243,982 A * | 9/1993 | Möstl et al. ............... 128/632 |
| 5,386,833 A | 2/1995 | Uhen ..................... 73/23.3 X |
| 5,616,822 A * | 4/1997 | Griffiths et al. ............ 73/1.06 |
| 5,826,577 A | 10/1998 | Peroz, Jr. et al. |

FOREIGN PATENT DOCUMENTS

WO    WO 99/46572 A1 *   9/1999   ............ G01M/3/20

OTHER PUBLICATIONS

Pulmonary Function Testing Guidelines and Controversies, Chapter 16, Antonius L. Van Kessel, B.S., RCPT p. 165–185, Copyright© 1982 by Academic Press, Inc. Month Not Given.

* cited by examiner

Primary Examiner—Thomas P. Noland
(74) Attorney, Agent, or Firm—John C. McMahon

(57) ABSTRACT

A calibration apparatus for checking the accuracy of DLco testing machines includes a pair of syringes mounted side by side in a frame and joined by a valve controlled gas passageway to a coupling adapted to mate with the testing machine. The first syringe receives gas from the testing machine and the second syringe has a chamber from which gas of a known concentration is returned to the testing machine. The chamber of the second syringe is flow connected by a valve to a source of test gas. The gas passageway is constructed in such a manner to reduce dead air space and to allow purging with test gas to eliminate contamination with ambient air or gas of previous tests.

15 Claims, 2 Drawing Sheets

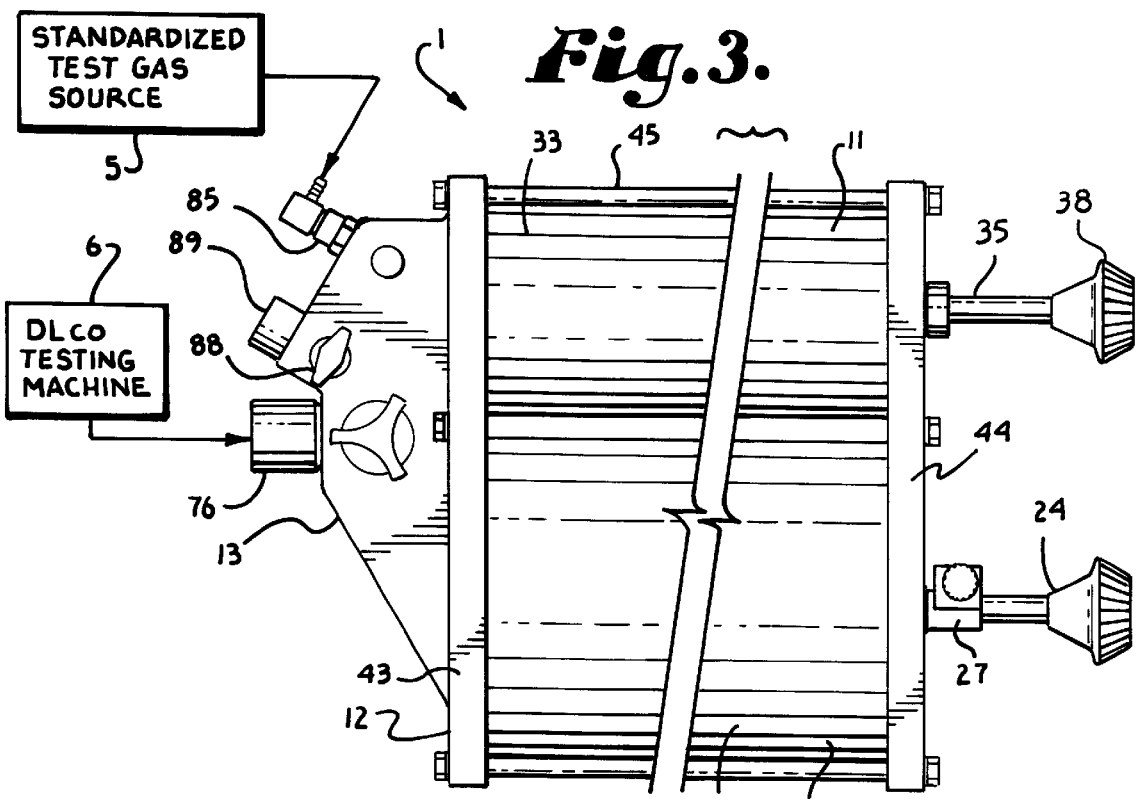
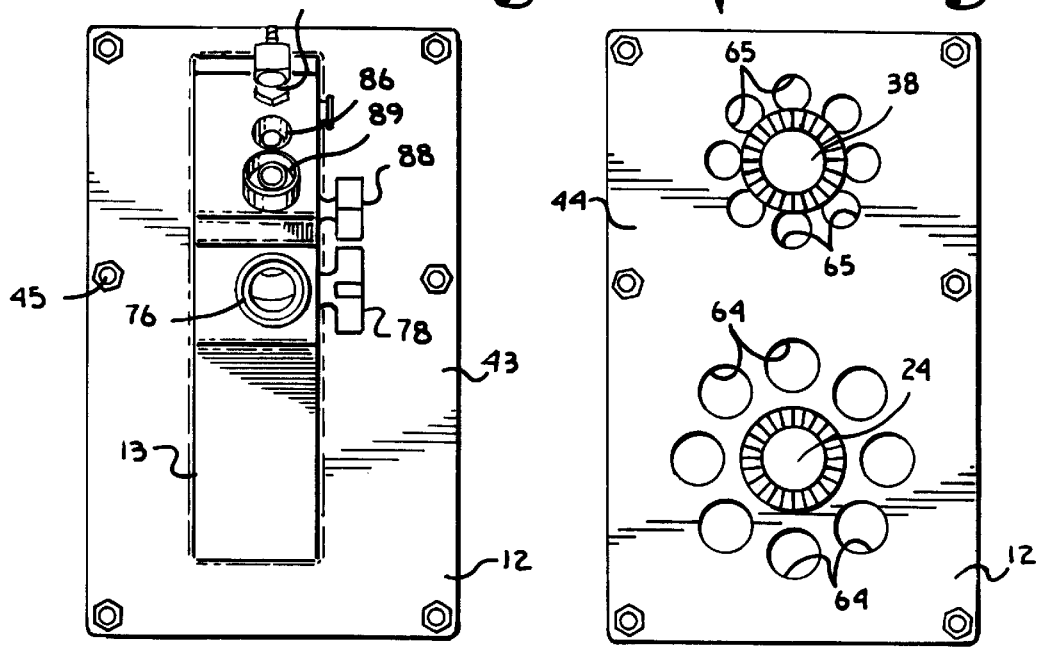

DLCO CALIBRATION SYRINGE APPARATUS

BACKGROUND OF THE INVENTION

The present invention is directed to a calibration apparatus for allowing the user of a DLco testing machine to check the ability of the machine to correctly measure carbon monoxide levels in a gas sample.

There are many different types of tests that are available to today's medical practitioners and pulmonary rehabilitation practitioners for testing various functions of the lung. Many types of diseases, such as emphysema, and injuries reduce the ability of gasses to transfer across the membrane that separates the interior gas spaces of the lungs from the pulmonary-capillary system. This membrane is often referred to as the alveolar-capillary membrane.

A number of somewhat related tests have been developed in order to test the function of this membrane without invasion into the lung by surgery or apparatus. These non-invasive tests take advantage of the manner in which carbon monoxide transfers across the membrane and in general measure the rate at which carbon monoxide diffuses across the human lung. The rate of carbon monoxide diffusion then provides the testor with information as to diffusion of other gasses, especially oxygen and carbon dioxide. Because the carbon monoxide reacts in certain ways with the hemoglobin, concentrations of the carbon monoxide in the blood (at least at the levels utilized in testing) are not relevant and a practitioner can calculate the diffusion of carbon monoxide across the membrane by knowing such factors as the initial concentration of carbon monoxide in the lungs, an elapsed time, and the final concentration of the carbon monoxide after the elapsed time. Such tests allow the calculation of a gas transfer factor for carbon monoxide which is generally referred to as the pulmonary diffusing capacity (DLco). While one principal testing technique is used for determining this factor, other techniques have been used in the past, have been proposed or may be developed in the future.

Various types of machines have been developed for conducting the pulmonary diffusion capacity test. Such machines typically deliver a known quantity of a test gas with known concentrations of various components to a patient wherein the test gas includes a small non-harmful and specific initial concentration of carbon monoxide, along with a tracer gas that does not cross the lung membrane and allows a user to calculate dilution of the test gas in the lungs. Some DLco testing machines require that the person being tested take several breaths from the machine before the testing begins to start programming. Other machines provide only a single test breath. Subsequently to receiving a test breath from the machine, the patient breathes out or exhales the gas that has been received from the machine back into the machine after a specific elapsed period of time. The machine then performs certain analysis on the test gas exhaled by the patient, normally to determine fairly accurately the exhaled concentration of carbon monoxide which will be less than the inhaled concentration since some will cross the lung membrane.

The present invention is not directed to the machine that delivers the test gas to the patient and receives the subsequent exhaled gas for analysis, but rather to an apparatus for testing the machine to insure that it is correctly analyzing the exhaled gasses. In order to check the calibration of the testing machine to determine whether it is accurate in measuring the carbon monoxide concentration in the exhaled gasses, it is important to mimic the testing procedure as much as possible in order to locate and identify problems not only with the carbon monoxide analyzer, but with the procedure for delivering the gas to the carbon monoxide analyzer.

While simply delivering a gas stream of a predetermined concentration of carbon monoxide to the carbon monoxide analyzer of the machine allows a technician to determine whether or not the machine can accurately determine the carbon monoxide concentration, such a test does not take into account other factors which may affect the analyzed carbon monoxide concentration when the test is run in a true medical environment with a patient. For example, it may be found that the testing machine is not correctly receiving the exhaled gas from the patient or that the tubing to the testing machine is too long and contains too much extraneous gas which then dilutes the gas sample, so as to provide an inaccurate analysis.

Consequently, it is important for the calibration apparatus to both provide a standardized gas of known carbon monoxide concentration, but also to provide the gas in a manner that is as realistic to the actual use with a patient as possible in order to insure that other factors do not cause the tester to incorrectly analyze the carbon monoxide gas concentration.

SUMMARY OF THE INVENTION

A DLco calibration syringe apparatus is provided for calibrating and insuring the accuracy of pulmonary testing machines that allow a patient to inhale a gas containing a low percentage of carbon monoxide and then, subsequently, receive back and analyze the exhaled gas from the patient to determine the percentage concentration of carbon monoxide after a given time period or sequence of events. The calibration apparatus includes a pair of adjacent syringes joined on one end by a gas flow passage that also communicates during use with the DLco testing machine. Flow through the gas passageway is controlled by a multi-position valve. The first of the syringes includes a piston slideably mounted in a chamber that is joined to the gas flow pathway and which receives a quantity of gas from the testing machine upon proper positioning of the valve. The receipt of the gas from the testing machine by the first syringe is designed to simulate inhalation of a breath by a patient of a predetermined amount of gas having a preselected concentration of carbon monoxide. The first syringe is calibrated by volume and may be utilized to simulate taking and delivering several breaths from the machine in a pre-breathing mode required by certain of such machines.

The second syringe also includes a cylinder with a piston mounted therein so as to form a chamber in communication with the gas flow passageway. The second chamber is filled with a quantity of test gas wherein the percentage concentration of at least the carbon monoxide in the test gas is known and, preferably, all of the concentrations of the components of the test gas are known with some precision. Normally, the remainder of the gasses in the test gas will include an inert gas that generally does not cross the lung membrane, such as methane, neon or helium and will have a concentration of oxygen similar to ambient air. The test gas may have other gasses in concentrations found in typical exhaled breaths. After a given period of time, for example, ten seconds, or after a series of events occurs, the valve in the gas passageway is routed so as to communicate the second syringe with the test machine and the syringe is operated by a user to discharge the test gas therein into the testing machine.

The apparatus also includes a fill system joined with a test gas sample tank that can be selectively flow connected with the second syringe chamber by the person administering the test, as well as a bleed valve to allow some of the test gas to pass through the gas passageway to purge other gasses positioned therein and a relief valve to prevent the second syringe from being over-pressurized.

OBJECTS AND ADVANTAGES OF THE INVENTION

Therefore, the objects of the present invention are: to provide a syringe calibration apparatus for calibrating DLco testing machines comprising a pair of closely mounted syringes having internal pistons slideably mounted within a cylinder to form a variable volume chamber therein; to provide such an apparatus wherein the internal chambers of the syringes are joined by a flow controllable gas passageway with each other and with the testing machine during usage; to provide such an apparatus wherein the first of the syringes is sized and shaped to receive a preselected volume of gas from the testing machine and the second syringe is sized and shaped to return a preselected volume of test gas to the testing machine with a preselected concentration of carbon monoxide; to provide such an apparatus wherein the gas flow passageway has relatively very little dead space between the second syringe and the test machine; to provide such an apparatus wherein the gas flow passageway provides a purge valve to allow purging of the passageway with test gas prior to usage; to provide such an apparatus wherein the first syringe chamber is operably joined with a supply of test gas under control of a fill valve; to provide such an apparatus wherein the syringe that receives gas from the test machine can be set to receive varying amounts of gas and designed to allow an operator to return the gas from the cylinder to the machine in certain pre-breathing modes; and to provide such a calibration apparatus which is relatively inexpensive to produce, easy to use, and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a fragmentary side elevational view of the syringe calibration apparatus.

FIG. 4 is a front elevational view of the syringe calibration apparatus.

FIG. 5 is a rear elevational view of the syringe calibration apparatus.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
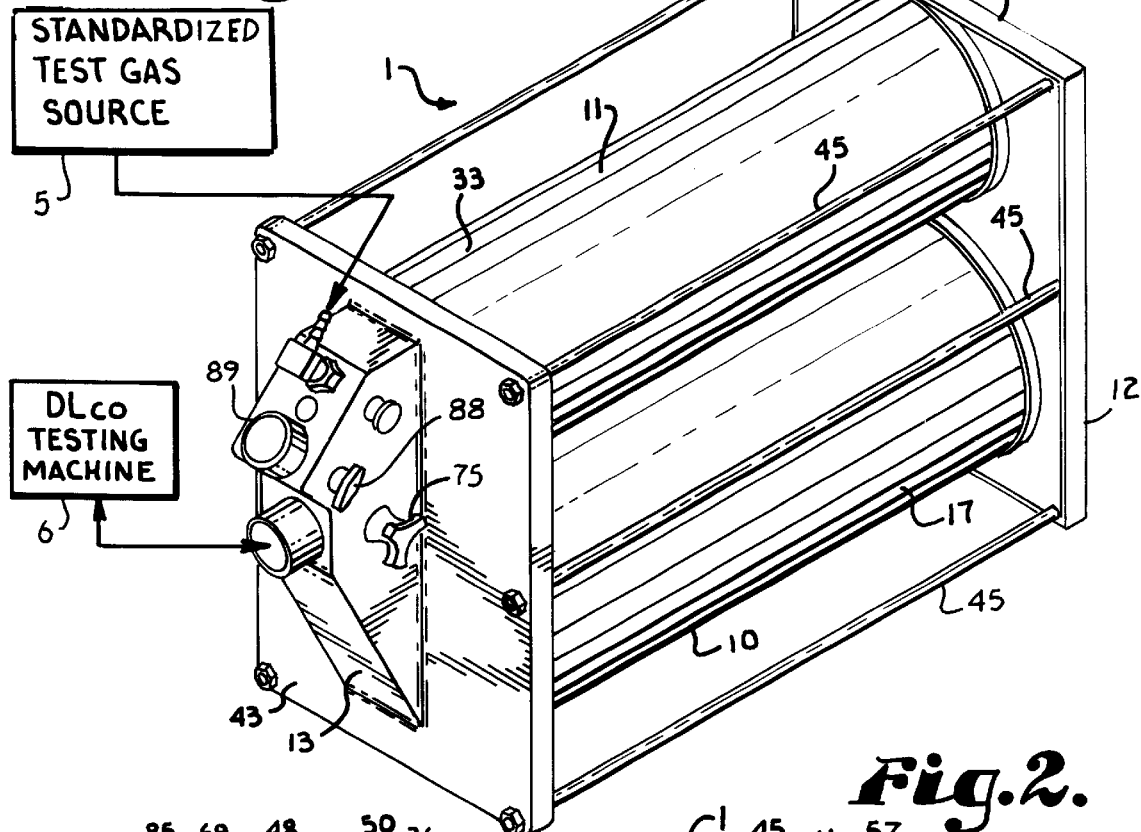
FIG. 1 is a perspective view of a DLco syringe calibration apparatus in accordance with the present invention shown schematically joined with a test gas source and with a DLco testing machine.

The reference number 1 generally indicates a calibration apparatus in accordance with the present invention. The calibration apparatus 1 is illustrated in FIG. 1 as schematically joined to a standard test gas source 5 and a DLco testing machine 6.

The calibrating apparatus 1 includes a first syringe 10 and a second syringe 11 mounted in a frame 12 with a gas manifold 13 located on the front of the frame 12.

The first syringe 10 includes a cylindrical shaped body 17 within which is mounted a piston 18. The piston 18 includes a sealing member 19 around the perimeter thereof and is sized and shaped to slide within the interior surface 20 of the cylindrical member 17 in a manner such that the sealing member 19 seals as the piston 18 moves along the cylindrical member 17.

A rod 23 is centrally attached to the piston 18 and has an operator handle 24 located opposite the piston 18 an external of the cylindrical member 17. The rod 23 both provides stability to the piston 18 and allows an operator to position the piston 18 within the cylindrical member 17. The rod 23 includes a first fixed stop 26 which limits the range of motion of the piston 18 within the cylindrical shaped member 17 for purposes of stability. The rod 23 also has positioned thereon an adjustable second stop 27 which is positionable therealong to allow a user to select an initial position for the piston 18 within the cylindrical member 17. Located along the rod 23 is a calibrated rule 26 that allows a user to visually and accurately determine the position of the piston 18 relative to the cylindrical member 17.

The second syringe 11 also includes a cylindrical member 33 within which is mounted a piston 34 with a stabilizing and position adjusting rod 35. The rod 35 is mounted and secured to the center of the piston 34 and extends through the frame 12, as will be discussed below. The piston 34 also includes a circumferential and peripheral sealing O-ring 36 that seals with the cylindrical member 33 during use. The rod 35 includes a stop 37 to limit the maximum position to which the piston 34 may move within the cylindrical member 33 and an operator handle 38 located opposite the piston 34 outside of the cylindrical member 33.

The frame 12 comprises a front plate 43 and a rear plate 44 joined by six tie rods 45 located in opposing corners of the front plate 43 and rear plate 44 and between the cylindrical members 17 and 33. The front plate 43 includes a first recess 47 that is sized and shaped to snugly receive the cylindrical member 17 and a second recess 48, which is likewise sized and shaped to receive the cylindrical member 33. Sealing O-rings 49 and 50 also are positioned about the cylindrical members 17 and 33 respectively, and seal with the recesses 47 and 48 respectively. The rear plate 44 also includes a pair of recesses 54 and 55. The recess 54 is sized and shaped to snugly receive the cylindrical member 17 and includes an O-ring 56 for purpose of stability. Likewise the recess 55 is sized and shaped to receive the cylindrical member 33 and also includes an O-ring 57 for stability. The rear plate 44 also has apertures 60 and 61 therein which are aligned to slideably receive the rods 23 and 35 respectively. Positioned around the aperture 60 is a series of vent openings 64 passing horizontally through the rear plate 44 and connecting the rear interior of the cylindrical member 17 with ambient air. Likewise positioned around the aperture 61 are a series of vent openings 65.

Figure 2:
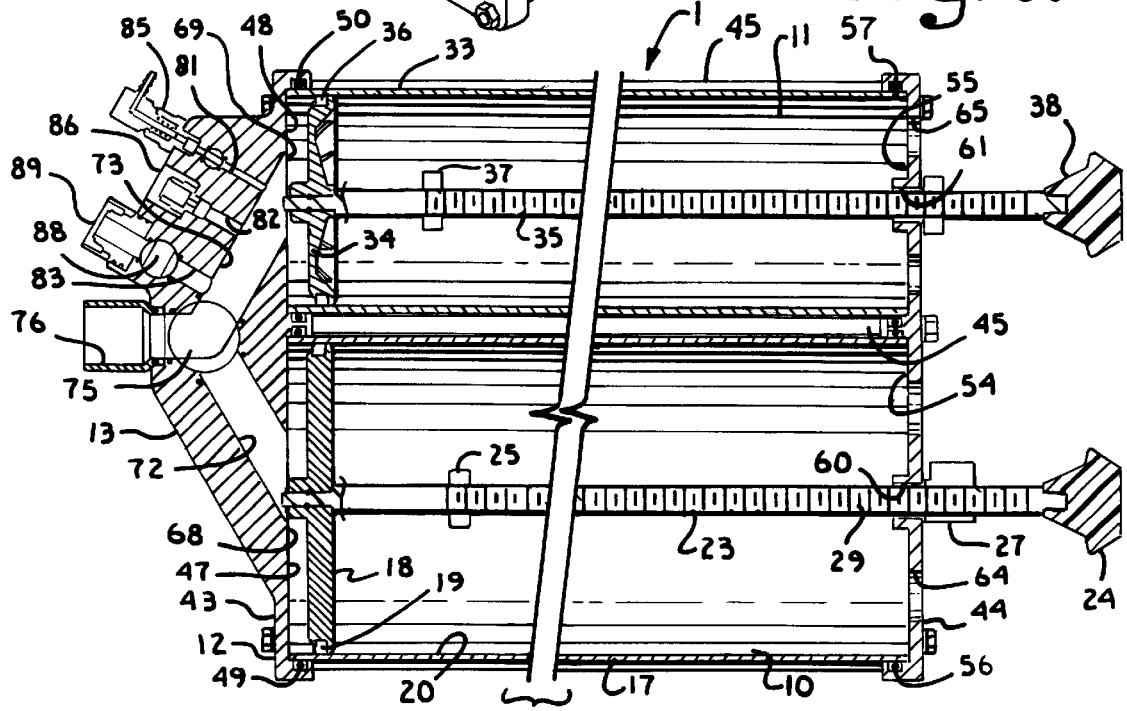
FIG. 2 is a cross-sectional view of the calibration syringe apparatus, taken along the line 2—2 of FIG. 1.

The front plate 43 in the illustrated embodiment is integrally formed with the gas manifold 13, although it is foreseen that the two elements could be manufactured separately. The front plate 43 functions in cooperation with the pistons 18 and 34 and their associated cylindrical members 17 and 33 to form variable sized chambers 68 and 69 respectively. When the pistons 18 and 34 are positioned as close to the gas manifold 13 as possible and to the left as seen in FIG. 2, the chambers 68 and 69 are relatively very small in volume and the volume of the chamber 69 preferably approaches a zero volume as closely as possible when the piston 34 is near the manifold 13. As the pistons 18 and 34 move away from the gas manifold 13 and to the rear or right, as seen in FIG. 2, the chambers 68 and 69 grow in volume and function to receive selected gasses therein.

The gas manifold 13 extends forward of the front plate 43, as is seen in FIGS. 1, 2, and 3. The gas manifold 13 includes a first gas passageway 72 and a second gas passageway 73 joined at a frontward end thereof by a multi positional valve 75. Ends of the passageways 72 and 73 opposite the valve 75 operably flow connect with the chambers 68 and 69 respectively. The valve 75 is also flow connected with a forward projecting coupling 76 that is sized and shaped to join with the gas discharge and receiving nozzle of a DLco testing machine 6. In this manner, the valve 75 may be set to allow flow from the testing machine 6 to the chamber 68 or alternatively, to allow flow from the chamber 69 to the testing machine 6. The valve 75 includes an operator control knob 78.

Third, fourth and fifth gas passageways 81, 82, and 83 also flow connect with the second gas passageway 73, as is shown in FIG. 2. The third gas passageway 81 is joined with a quick operating flow control valve 85 mounted on the front of the gas manifold 13. The valve 85 also operably flow connects with the standardized test gas source 5 during use and operably provides for an operator using gas from the source 5 to fill the chamber 69 by depression of the valve 85.

The fourth gas passageway 82 is joined to a relief valve 86 also mounted on the gas manifold 13 to safely relieve over-pressure in the chamber 68, should the chamber 68 inadvertently become over-pressurized. Furthermore, the fifth gas passageway 83 is joined by a valve 88 to a vent 89 mounted on the front of the gas manifold 13. The operation of the valve 88 and vent 89 function to allow a user to purge gas that enters the chamber 69 through the valve 85 and also through the second gas passageway 73 in order to assure that the gas in the second gas passageway 73 has a composition that is essentially consistent with the gas composition in the chamber 69.

In use the calibration apparatus 1 is joined to any of numerous types of DLco testing machines, such as are illustrated by the block 6 and to a source 5 of standardized test gas. The calibration apparatus 1 is then utilized much to mimic testing with a patient. In particular, the DLco testing machine will normally discharge a quantity of test gas into the patient, sometimes after offering several breaths of normal air to the patient in order to start machine programming or in other cases without such pre-breathing.

For pre-breathing, the operator manipulates the piston 18 in the syringe 10 to mimic breathing by a patient. The test gas will be similar in composition to air which may be humidified or otherwise treated to make it similar to a normal breath composition and which will include a small concentration of carbon monoxide, as well as a known quantity of an inert tracer gas. The carbon monoxide concentration may be varied with subsequent tests to insure the machine 6 is able to correctly analyze carbon monoxide from a range of patients who have different membrane diffusion, such as athletes and persons with emphysema. The valve 75 is initially set to allow the gas from the testing machine 6 to enter or flow into the chamber 68 through the first passageway 72. The piston 18 moves away from the gas manifold 13 as gas enters the chamber 68 thereby enlarging the chamber 68. The piston 18 may be pre-positioned relative to the cylindrical member 17 away from the gas manifold 13 by location of the second stop 27 therealong. Such positioning will be in accordance with the particular testing being conducted.

Once the gas has been delivered from the testing machine 6 to the chamber 68, either an elapsed time, such as 10 seconds, is allowed to occur or some series of events is allowed to occur, after which an exhalation of gas into the testing machine 6 occurs.

In particular, a quantity of a test gas with a known concentration of carbon monoxide, which is lower than the concentration of carbon monoxide in the gas discharged by the testing machine 6, is placed in the chamber 68 by operation of the valve 85.

Normally, the chamber 68 will have several volumes, for example 250 milliliters of test gas delivered to it which is then discharged to purge the chamber 68 and gas manifold 13 prior to final filling for conducting the test. The gas in the chamber 68 causes the piston 34 to retract or move away from the gas manifold 13 a preselected distance or until the stop 37 engages the rear plate 44. The valve 88 and vent 89 may then be operated in such a manner as to discharge some of the gas entering through the valve 85 in such a manner as to sweep or purge the second passageway 73 and thereby remove any stagnant or gas remaining therein, such as ambient air or from a previous test, if a purge has not already been completed. In this way the gasses in both the chamber 69 and the second passageway 73 have essentially the same composition, especially with respect to concentration of carbon monoxide. Normally gas will be positioned within the chamber 69 before the calibration or testing is done, but this step could be taken subsequent to the discharge of gas from the machine 6.

Subsequent to the lapse of a given period of time or a series of events, the valve 75 is set to flow connect the coupling 76 with the second passageway 73. The piston 34 is then urged toward the front of the cylindrical member 33, that is toward the gas manifold 13, by an operator pushing on the handle 38. This urges the gas that is then in the chamber 69 out of the chamber 69 due to compression of the chamber 69 and through the second passageway 73 to the DLco testing machine 6. The DLco testing machine then performs one or more analyses on the test gas to determine whether the DLco machine is correctly analyzing the concentration of carbon monoxide in the gas and/or whether there are any other problems associated with the system that cause the machine 6 to incorrectly analyze the carbon monoxide concentration within the test gas.

The coupling 76 is mounted as close to the valve 75 as possible, such that dead space, that could hold contaminated or ambient air is reduced to a minimum between the DLco testing machine 6 and the apparatus 1. Because the second gas passageway 73 is purged with test gas and the chance for contamination at the coupling 75 is reduced as much as possible, the gas analyzed by the testing machine 6 has very little likelihood of being contaminated or diluted with ambient air or other gas in the calibrating apparatus 1.

It is to be understood that while certain forms of the present invention have been illustrated and described herein, it is not to be limited to the specific forms or arrangement of parts described and shown.

What is claimed and desired to be secured by Letters Patent is as follows:

1. A calibrating apparatus for operatively testing the accuracy of a DLco testing machine; said calibrating apparatus comprising:
   a) a frame;
   b) a first syringe with a first movable piston forming a first gas receiving chamber of variable size;
   c) a second syringe with a second movable piston forming a second gas receiving chamber of variable size; and
   d) a gas manifold selectively flow connecting to said first and second chambers and during operation of said apparatus being adapted to flow connect with the testing machine; said manifold including a single multiple position valve that selectively flow connects said first and second syringes with said manifold; said manifold also including a coupling for flow connecting with the testing machine; said valve and said coupling being in close proximity to one another to minimize contamination of test gas from said second syringe by residual gas in said manifold during use.

2. The apparatus according to claim 1 wherein:
   a) said first and second syringes are mounted side by side in close proximity to one another.

3. The apparatus according to claim 1 wherein:
   a) said manifold includes a gas passageway flow connecting said second gas receiving chamber with a coupling sized and shaped to mate with the DLco testing machine; and
   b) said passageway including the multiple position valve.

4. The apparatus according to claim 1 wherein:
   a) said manifold includes a first gas passageway flow connecting with said first chamber and a second gas passageway flow connecting to said second chamber;
   b) said first and second passageways being joined at the multiple position valve such that said valve selectively controls flow through alternative ones of said passageways; and
   c) said passageways being selectively flow connected through said valve to a coupling sized and shaped to be adapted during use to mate with the DLco testing machine.

5. A calibrating apparatus for operatively testing the accuracy of a DLco testing machine; said calibrating apparatus comprising:
   a) a frame including a front plate;
   b) a first syringe with a first movable piston forming a first gas receiving chamber of variable size;
   c) a second syringe with a second movable piston forming a second gas receiving chamber of variable size;
   d) said first and second syringes each include a cylindrical member;
   e) said front plate includes first and second receivers; said receivers being sized and shaped to snugly receive respective cylindrical members; and
   f) a gas manifold selectively flow connecting to said first and second chambers and during operation of said apparatus being adapted to flow connect with the testing machine.

6. A calibrating apparatus for operatively testing the accuracy of a DLco testing machine; said calibrating apparatus comprising:
   a) a frame including a rear plate;
   b) a first syringe with a first movable piston forming a first gas receiving chamber of variable size;
   c) a second syringe with a second movable piston forming a second gas receiving chamber of variable size;
   d) said first and second syringes include first and second rods attached to pistons of each respectively; said first and second rods being received through apertures in said rear plate so as to extend outwardly therefrom; and
   e) a gas manifold selectively flow connecting to said first and second chambers and during operation of said apparatus being adapted to flow connect with the testing machine.

7. The apparatus according to claim 6 wherein:
   a) said rear plate includes vents therein associated with each of said syringes.

8. The apparatus according to claim 6 wherein:
   a) said first rod includes a first stop limiting rearward movement and spacing maximum rearward movement of said first syringe piston from a rear wall of said first syringe.

9. The apparatus according to claim 8 wherein:
   a) said first rod includes an adjustable second stop to limit forward movement of said first syringe piston relative to a rear wall of said first syringe.

10. The apparatus according to claim 9 wherein:
    a) said first rod is calibrated therealong to provide for accurate positioning of said second stop.

11. A calibrating apparatus for operatively testing the accuracy of a DLco testing machine; said calibrating apparatus comprising:
    a) a frame;
    b) a first syringe with a first movable piston forming a first gas receiving chamber of variable size;
    c) a second syringe with a second movable piston forming a second gas receiving chamber of variable size;
    d) a gas manifold selectively flow connecting to said first and second chambers and during operation of said apparatus being adapted to flow connect with the testing machine;
    e) said manifold includes a first gas passageway flow connecting with said first chamber and a second gas passageway flow connecting to said second chamber;
    f) said first and second passageways being joined at a valve such that said valve selectively controls flow through alternative ones of said passageways; and
    g) said passageways being selectively flow connected through said valve to a coupling sized and shaped to be adapted during use to mate with the DLco testing machine.

12. The apparatus according to claim 11 wherein:
    a) said coupling is positioned substantially adjacent to said valve to minimize dead gas space therebetween.

13. A calibrating apparatus for operatively testing the accuracy of a DLco testing machine; said calibrating apparatus comprising:
    a) a frame;
    b) a first syringe with a first movable piston forming a first gas receiving chamber of variable size;

c) a second syringe with a second movable piston forming a second gas receiving chamber of variable size;

d) a gas manifold selectively flow connecting to said first and second chambers and during operation of said apparatus being adapted to flow connect with the testing machine;

e) said manifold includes a gas passageway flow connecting said second gas receiving chamber with a coupling sized and shaped to mate with the DLco testing machine; and f) said passageway including a flow control valve located substantially adjacent to said coupling so as to minimize contamination of gas passing through said valve into said coupling with residual gas in said manifold.

14. The apparatus according to claim 13 wherein:

a) said gas passageway is flow connected to a test gas source valve that is in turn adapted during use to be connected to a source of test gas.

15. The apparatus according to claim including:

a) a vent joined to said gas passageway; said vent including a vent valve and being placed in close proximity to said control valve to allow purging of said passageway by opening of said vent valve.

* * * * *